United States Patent
Crawford

(10) Patent No.: US 6,544,251 B1
(45) Date of Patent: Apr. 8, 2003

(54) PERIPHERALLY INSERTED CATHETER

(76) Inventor: Michael K. Crawford, 631 Knipp Rd., Houston, TX (US) 77024

( * ) Notice: Subject to any disclaimer, the term of this patent is extended or adjusted under 35 U.S.C. 154(b) by 0 days.

(21) Appl. No.: 09/502,190

(22) Filed: Feb. 10, 2000

Related U.S. Application Data

(60) Provisional application No. 60/119,538, filed on Feb. 10, 1999.

(51) Int. Cl.[7] .............................................. A61M 25/16
(52) U.S. Cl. ...................................... 604/537; 604/523
(58) Field of Search ................ 604/506, 513, 604/93.01, 165.03, 167.01–167.05, 164.01, 174, 177, 178, 256, 264, 905, 523–525, 533, 537, 539, 538; 128/DIG. 26; 606/192, 194

(56) References Cited

U.S. PATENT DOCUMENTS

| | | | | |
|---|---|---|---|---|
| 3,768,476 A | * | 10/1973 | Raitto ......................... 128/275 |
| 3,903,895 A | * | 9/1975 | Alley et al. ............. 128/350 R |
| 3,924,632 A | * | 12/1975 | Cook .......................... 128/348 |
| 4,230,109 A | * | 10/1980 | Geiss ...................... 128/214 R |
| 4,329,987 A | * | 5/1982 | Rogers et al. .......... 128/214 R |
| 4,335,717 A | * | 6/1982 | Bujan et al. ............ 128/214 G |
| 4,364,383 A | * | 12/1982 | Vcelka ........................ 128/214 |
| 4,417,890 A | * | 11/1983 | Dennehey et al. .......... 604/256 |
| 4,493,696 A | * | 1/1985 | Uldall .......................... 604/43 |
| 5,573,521 A | * | 11/1996 | McFarlane .................. 604/282 |
| 5,624,413 A | * | 4/1997 | Markel et al. .............. 604/280 |
| 6,112,111 A | * | 8/2000 | Glantz ........................ 600/424 |

* cited by examiner

Primary Examiner—Brian L. Casler
Assistant Examiner—Cris L. Rodriguez
(74) Attorney, Agent, or Firm—Gary L. Bush; Andrews & Kurth, LLP

(57) ABSTRACT

An improved peripherally inserted catheter with its soft ferule including a "ball-like" structure between the soft exterior tube and the soft ferule. A clamp is also provided which is characterized by a clamping force sufficient to clamp the exterior soft tube but insufficient to crimp the inner tube of the ferule for the situation where the clamp were to creep onto the ferule. A sterile screw assembly is coupled to the end of the ferule in another arrangement.

1 Claim, 2 Drawing Sheets

PERIPHERALLY INSERTED CATHETER

CROSS REFERENCE TO RELATED APPLICATION

This application claims priority from Provisional application Ser. No. 60/119,538 filed on Feb. 10, 1999.

BACKGROUND OF THE INVENTION

1. Field of the Invention

This invention relates to improvements to peripherally inserted catheters. In particular, the invention relates to a method and apparatus for preventing damage to the catheter by a clamp used to prevent flow through a soft tube, which exits from a patient's limb.

2. Description of the Prior Art

Peripherally Inserted Catheters (called PICCs), like other types of intravenous catheters, are inserted through a vein in a patient's arm. The catheters often remain in place throughout the course of the patient's treatment and therapy.

A PICC catheter includes a long insertion tube 14, which is inserted into a specific vein at an intervention point near the bend of the patient's arm FIG. 1 of the drawings shows a prior art PICC 10 with an exterior soft tube 12 which communicates with the insertion tube 14 at a surgical tag device 16 which is stitched to the patient's arm at the insertion point. A soft ferule 18 covers the end of the exterior soft tube. The ferule 18 is a sleeve, which surrounds the exterior soft tube and includes a small diameter tube therein, which runs between an injection site device 20 at the end of the catheter and the exterior soft tube 18. A clamp 22 is provided about the exterior soft tube 12 to prevent fluid flow through the catheter 10 when medication is not being inserted into the catheter 10 or blood is not being taken from the catheter 10.

FIG. 2 illustrates a PICC inserted into a vein at an injection point of the patient. While not illustrated, certain catheters have two exterior soft tubes, which exit in a "Y" shape. One exterior soft tube is used to inject medication; the other to withdraw blood from the patient.

A problem exists with the prior art PICC of FIG. 1 in that the clamp 22 may ride or "creep" along the soft exterior tube 12 toward the larger diameter soft ferule 18 which forms a sleeve about the end of the exterior soft tube (as shown in FIG. 3). When the clamp 22 is engaged about the soft ferule 18 and the tube inside it, the clamp pinches or crimps the tube within the ferule or the end of the exterior soft tube at pinch point 24 with a high probability of permanently deforming or collapsing or even severing the soft tube or the tube within the ferule. In that situation, bacteria are provided with a path into the interior of the soft tube 12 and directly into the patient's body. As illustrated in FIG. 2, a bacteria path is provided directly into the patient's heart, thereby creating an exceptionally dangerous situation.

3. Object of the Invention

A primary object of the invention is to provide an improved PICC where its exterior soft tube clamp is prevented from sliding from the exterior soft tube onto the larger diameter ferule, thereby preventing possible permanent deformation, collapse or severing of the exterior soft tube.

SUMMARY OF THE INVENTION

The object identified above is incorporated in an improved PICC where its soft ferule includes a "ball-like" structure between the soft exterior tube and the soft ferule. The ball-like arrangement prevents the clamp from sliding from the exterior soft tube onto the soft ferule.

BRIEF DESCRIPTION OF THE DRAWINGS

The objects, advantages, and features of the invention will become more apparent by reference to the drawings which are appended hereto and wherein like numerals indicate like parts and wherein an illustrative embodiment of the invention is shown, of which.

DESCRIPTION OF THE INVENTION

Figure 1:
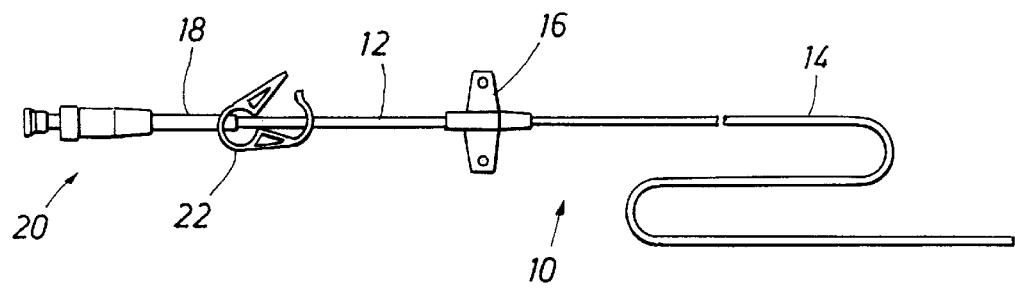
FIG. 1 illustrates a prior art PICC device.
Figure 2:
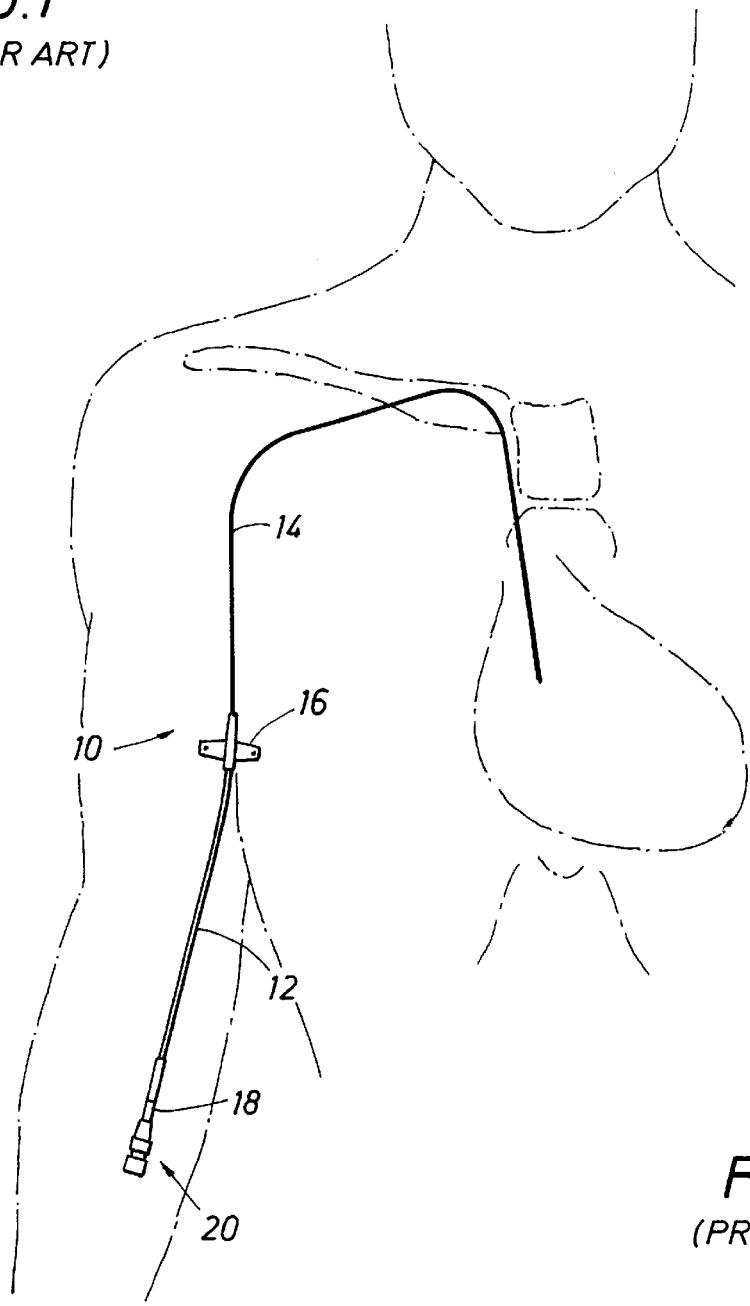
FIG. 2 illustrates a prior art PICC which has been inserted into a patient's body in the anticubital area of the arm (near the bend of patient's arm)
Figure 3:
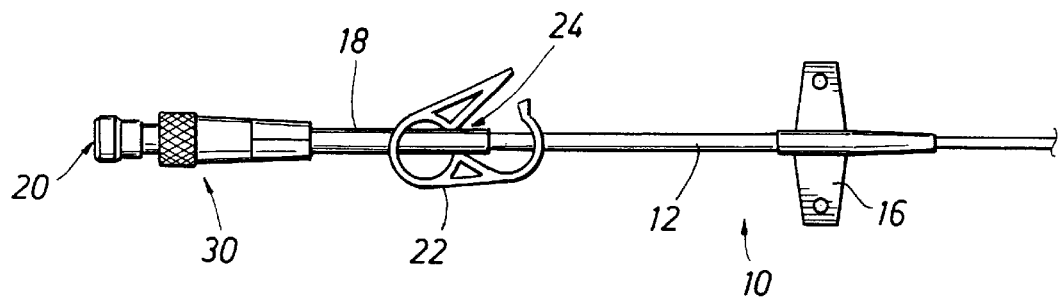
FIG. 3 shows a prior art PICC device where the clamp has slid or "crept" from the position on the exterior soft tube to a position about the soft ferule which covers the end of the soft tube.

FIG. 3 shows the prior art PICC 10 where the clamp 22 about the exterior soft tube 12 has worked its way or "crept" toward the needle/injection site 20 and about the soft ferule 18. The clamp pinch point 24 may collapse a small inner line (not illustrated), which runs through the ferule 18 to the exterior soft tube 12. Collapse, deformation, or severing of a path to the exterior soft tube 12 may allow bacteria to enter the vein or cause the obstruction to be forced open with liquid pressure which can cause damage to the heart.

Figure 4:
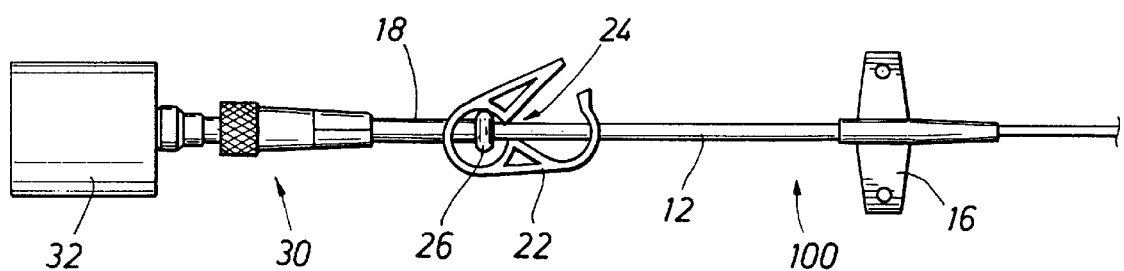
FIG. 4 illustrates an improved PICC with a device for prevention of the clamp about the exterior soft tube from sliding onto the soft ferule at the injection site.
Figure 5:
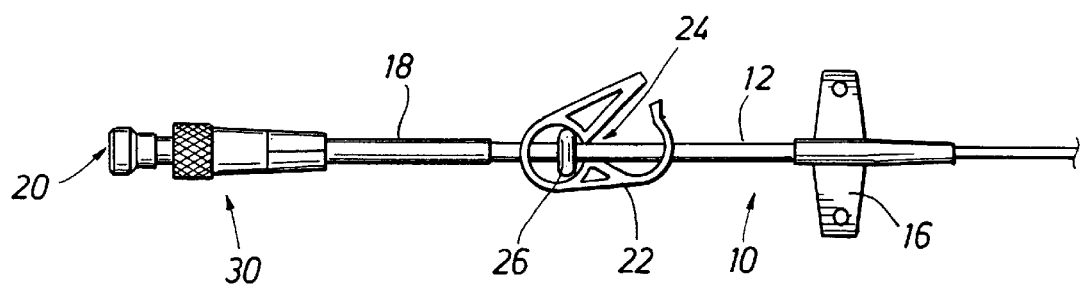
FIG. 5 illustrates an improved PICC with an enlarged radial section about the exterior soft tube which prevents a clamp from creeping onto the soft ferule.

FIG. 4 shows the invention of an improved PICC 100 where a ball-like structure 26 is provided about the end of the soft ferule 18 in order to prevent the clamp 22 from sliding from the exterior soft tube 12 to a position on the soft ferule 18. The ball 26 can be secured at a point on the exterior soft tube 12 or alternatively to the end of the ferule 26 in order to prevent the clamp 26 from sliding from the exterior soft tube 12 onto the ferule 18.

Alternatively, a clamp can be provided which does not have sufficient clamping force to crimp the small inner line inside the ferule, even if it is clamped about the soft ferule, yet has enough clamping force to clamp and prevent flow through the soft tube 12.

As shown in FIG. 3, the luer/injection site has in the past been designed to be used with a needle inject system 30. A needle is applied to the end of the PICC 10. Alternatively, according to the invention, a sterile screw fixture 32 is attached to the end of the PICC for insertion of medication and the like through the catheter, as illustrated schematically in FIG. 4.

What is claimed is:

1. A peripherally inserted catheter assembly including an exterior tube and a soft ferule secured to an end thereof at an attachment point, said soft ferule providing a flow path from an injection site to said exterior soft tube, an enlarged radial section provided on said exterior soft tube adjacent said attachment point of said soft ferule with said exterior soft tube, whereby a clamp disposed about said exterior soft tube is prevented from creeping onto said soft ferule by said enlarged radial section on said exterior surface.

* * * * *